(12) United States Patent
Schwarz et al.

(10) Patent No.: US 7,767,231 B2
(45) Date of Patent: Aug. 3, 2010

(54) TASTE-MASKING PHARMACEUTICAL COMPOSITIONS

(75) Inventors: Franz Xaver Schwarz, Wörgl (AT); Irina Kosilek, Kufstein (AT)

(73) Assignee: Sandoz AG, Basel (CH)

( * ) Notice: Subject to any disclaimer, the term of this patent is extended or adjusted under 35 U.S.C. 154(b) by 426 days.

(21) Appl. No.: 11/576,890

(22) PCT Filed: Oct. 10, 2005

(86) PCT No.: PCT/EP2005/010890

§ 371 (c)(1),
(2), (4) Date: May 18, 2007

(87) PCT Pub. No.: WO2006/040112

PCT Pub. Date: Apr. 20, 2006

(65) Prior Publication Data

US 2008/0008765 A1 Jan. 10, 2008

(30) Foreign Application Priority Data

Oct. 12, 2004 (GB) .................................. 0422645.2

(51) Int. Cl.
*A61K 9/50* (2006.01)
*A61K 31/7048* (2006.01)
*A61K 9/16* (2006.01)

(52) U.S. Cl. .................... 424/493; 424/490; 514/29

(58) Field of Classification Search ................. None
See application file for complete search history.

(56) References Cited

U.S. PATENT DOCUMENTS

| 3,922,379 | A | 11/1975 | Farhadieh |
|---|---|---|---|
| 4,808,411 | A | 2/1989 | Lu et al. |
| 4,853,229 | A * | 8/1989 | Theeuwes .................... 424/455 |
| 4,865,851 | A | 9/1989 | James et al. |
| 4,994,260 | A | 2/1991 | Kallstrand |
| 5,409,711 | A | 4/1995 | Mapelli |
| 5,609,909 | A | 3/1997 | Meyer |
| 5,730,997 | A | 3/1998 | Lienhop |
| 6,565,877 | B1 | 5/2003 | Mukherji |
| 2003/0054037 | A1 * | 3/2003 | Babcock et al. ............. 424/486 |

(Continued)

FOREIGN PATENT DOCUMENTS

EP 0 943 341 A1 9/1999

(Continued)

OTHER PUBLICATIONS

Erstad. Pharmacotherapy. 2003; 23 (9), posted Sep. 18, 2003.*

(Continued)

*Primary Examiner*—Shanon A Foley
(74) *Attorney, Agent, or Firm*—Luedeka, Neely & Graham, P.C.

(57) ABSTRACT

The present invention relates to a pharmaceutical composition for oral administration suitable for the preparation of a ready-to-use suspension comprising coated particles comprising an active substance having an unpleasant and/or bitter taste, such as clarithromycin, and a suspension base comprising an osmotically active substance capable of providing a high osmolality to the admixture of the suspension base with an aqueous suspending medium in the ready-to-use suspension. Said ready-to-use suspension maintains its palatability over a prolonged period of time by those defined osmotic conditions.

19 Claims, 2 Drawing Sheets

U.S. PATENT DOCUMENTS

| | | |
|---|---|---|
| 2004/0142029 A1 | 7/2004 | Becourt et al. |
| 2004/0175418 A1 | 9/2004 | Ferguson |
| 2005/0244339 A1* | 11/2005 | Jauernig et al. ............... 424/45 |

FOREIGN PATENT DOCUMENTS

| | | |
|---|---|---|
| WO | WO94/05260 | 3/1994 |

OTHER PUBLICATIONS

Tanigake A. et al: The bitterness intensity of clarithromycin evaluated by a taste sensor. Chem. Pharm. Bull. 51(11), 1241-1245 (2003) abstract.

Shimano K. et al: Evaluation of temperature-sensitive and drug dissolution properties of polyvinylacetal diethylaminoacetate gel. Yakzuaigaku (1994), 54(2), 69-76 (abstract).

Lu M.Y.F. et al: A polymer carrier system for taste masking of macrolide antibiotics. Pharm. Res. (1991), 8(6), 706-12 (abstract).

JP 02279622 Koyama I. et al., abstract.

* cited by examiner

TASTE-MASKING PHARMACEUTICAL COMPOSITIONS

This application is the National Stage of International Application No. PCT/EP2005/010890, filed on Oct. 10, 2005, which claims benefit under 35 U.S.C. §119(a)-(d) or (f) or 365(b) of foreign application, GB 0422645.2, filed on Oct. 12, 2004, the contents of both are incorporated herein by reference in their entirety.

FIELD OF THE INVENTION

The present invention relates to a pharmaceutical composition for oral administration comprising coated particles comprising an active substance which has an unpleasant and/or bitter taste when orally administered. More particularly, the present invention relates to a pharmaceutical composition comprising taste-masked coated particles comprising a macrolide antibiotic, preferably clarithromycin, which is in the form of a suspension which maintains its palatability over a prolonged period of time by means of defined osmotic conditions. Furthermore, the present invention relates to a process for preparing said composition.

BACKGROUND OF THE INVENTION

The oral administration of pharmaceutically active substances in conventional solid forms such as tablets or capsules is often problematic in special patient groups who have difficulties in swallowing said solid forms whole, for example children and older patients. For these patients, suitable dosage forms for drugs may be e.g. liquid forms, e.g. solutions, suspensions, syrups or emulsions, or alternative solid forms such as chewable tablets, effervescent tablets or soluble tablets. These dosage forms usually do not prevent a perceptible degree of exposure of the active substance to the taste buds, which is a major problem when the active substance has a unpleasant and/or bitter taste. In such cases, the active substance has to be taste-masked, so that the dosage form becomes palatable, thereby reducing the risk that the patients refuse to take the medicament.

It is a great challenge to taste-mask extremely bitter tasting active substances such as macrolides, e.g. erythromycin or clarithromycin, especially when comprised in suspensions. Conventional taste masking techniques such as the addition of sweeteners such as sugar, artificial sweeteners, fruit aromas, thickeners and amino acids, often fail to give the pharmaceutical composition an acceptable taste.

It is mostly that portion of the active substance in such dosage forms which is dissolved in the saliva and/or in the liquid for administration that generates the unpleasant taste. To overcome this problem, it is common to influence the solubility of said active substance in such a way that only a small portion of said substance, or even none of it, will dissolve in a suspension, or in the mouth. This is often achieved by embedding the bitter tasting active substance in a special embedding material or by coating said drugs. These techniques have, however, their limitations and usually prove effective only for moderately bitter drugs. The embedding and/or coating techniques may also adversely impact the desired release of the active substance into the digestive tract to achieve good bioavailability.

To ensure sufficient bioavailability of the active substance, one may use coatings, e.g. lipid and/or wax coatings that retard the dissolution of the active substance for a short period of time, or slightly retarding polymer films or the like. These coatings, however, can only provide satisfactory taste-masking if said suspensions are administered shortly after their reconstitution, i.e. after dispersion in an aqueous medium.

International Application WO 93/12771 discloses another technique for taste masking by coating core particles comprising e.g. clarithromycin with a polymeric coating layer comprising a prolamine fraction derived from grain proteins, preferably zein, and plasticizers being preferably fatty acids, wherein said coating layer is relatively thick.

Another technique is described in International Application WO 00/76479 A1, wherein the bitter tasting active substance is embedded in a taste-masking matrix composed of a combination of two enteric polymers, i.e. a methacrylic acid copolymer and a phthalate polymer, which is optionally coated.

Most of the conventional taste masking techniques fail to provide satisfactory taste masking in a suspension which is required to maintain its pleasant taste over an extended period of time, e.g. for at least 1 to 2 weeks as a reconstituted suspension. In such cases, film-coatings with a pH-related solubility are commonly used. This means that the pH value in the suspension is adjusted to a value at which the film-forming component, e.g. the film-forming polymer, comprised in the film-coating is not soluble. The pH value changes upon administration, and depending on the coating material used, the active substance will be released either into the stomach in the case that the coating is acid-soluble, or into the intestines, e.g. the small intestine, in the case of base-soluble enteric or gastro-resistant coatings.

International Application WO 91/16043 discloses the application of a polymeric coating being soluble only at a pH of 5 or greater to a core particle, and the addition of an acidic compound to the formulation to reduce or prevent the dissolution of the coating membrane in the oral cavity.

The proportioning of said film-coatings is, however, critical: film-coatings which are too strong and/or thick, may retard the rate of the drug release in the gastrointestinal tract to an extent which would be unacceptable for conventional immediate release formulations.

Another problem is that the above mentioned film coatings, e.g. polymer coatings, are never entirely "leak-proof", which means that even with intact film coatings a portion of the active substance is always released from the coated particles by way of diffusion into the suspension, which herein is called "leakage". This may lead to the sensation of a bitter taste after ingestion.

Generally, the pH value of the liquid component of pharmaceutical compositions such as suspensions is adjusted to a value that will ensure that the coating will not be dissolved and/or etched. However, if the taste-masked active substance possesses a good solubility in this pH range, this will, in turn, increase the diffusion of the unpleasant-tasting active substance and thereby cause leakage into the suspension and/or in the mouth after oral administration.

Additionally, conventional techniques for preparing a palatable liquid dosage form comprising an unpleasant and/or bitter tasting drug may involve costly and complicated preparative methods.

Accordingly, it is an object of the present invention to provide a liquid dosage form, particularly a suspension, comprising coated particles containing an unpleasant and/or bitter tasting pharmaceutically active substance, which is palatable and which keeps its palatability even over a prolonged period of time after being reconstituted e.g. by the addition of water. Additionally, said suspension should exhibit satisfactory bioavailability, i.e. a rapid release of the active substance in the gastro-intestinal tract after oral administration.

SUMMARY OF THE INVENTION

The present inventors have surprisingly found that the taste of the suspension can be considerably improved through adjusting the osmolality within the reconstituted suspension, more specifically, of the admixture of the suspension base mixed with an aqueous suspending medium, to a high level of not less than about 2000 mosmol per kg of suspending medium, for example per liter of water, and maintaining the osmolality within the specified range. This can be achieved by adding the herein described "osmotically active" substances to the suspension base. The high osmolality thereby obtained when said suspension base is mixed with an aqueous suspending medium presumably reduces the leakage of the active substance from the coated particles suspended in the ready-to-use suspension after reconstitution with e.g. water.

Thus, in one aspect, the invention provides a pharmaceutical composition for oral administration suitable for the preparation of a ready-to-use-suspension comprising a) coated particles comprising at least one pharmaceutically active substance having an unpleasant and/or bitter taste and optionally at least one excipient, and b) a suspension base comprising at least one osmotically active substance which is capable of providing a high osmolality to the admixture of said suspension base with an aqueous suspending medium in the ready-to-use suspension, and c) optionally at least one pharmaceutically acceptable excipient, wherein said high osmolality is not less than 2000 mosmole per kg of the suspending medium.

Preferably, the coated particles are taste-masked.

Preferably, the aqueous suspending medium is water.

Preferably, the osmolality of the admixture of the suspension base with an aqueous suspending medium is not less than 2500 mosmol per kg of suspending medium, e.g. per liter of water.

Preferably, the osmolality of the admixture of the suspension base with an aqueous suspending medium is from about 2500 to about 3500 mosmol per kg of suspending medium, e.g. per liter of water.

Preferably, the osmotically active substance is selected from the group consisting of sucrose, erythritol, xylitol, sorbitol, maltodextrin, cyclodextrin, potassium phosphate, sodium phosphate, sodium sulphate and sodium chloride, and mixtures thereof. Most preferably, the "osmotically active" substance is sucrose.

Preferably, said coated particles comprise a functional coating, more particularly, a functional coating which is semipermeable. Preferably, the coating is an enteric coating, i.e. gastro-resistant coating.

The active substances comprised in the coated particles are preferably macrolide antibiotics such as erythromycin and its derivatives, clarithromycin, azithromycin or roxithromycin, most preferably clarithromycin.

The invention provides furthermore a pharmaceutical composition for oral administration in the form of a ready-to-use suspension as described above which is preferably essentially free of acidic or basic additives.

In a further aspect, the invention provides a process for preparing a pharmaceutical composition for oral administration suitable for the preparation of a ready-to-use-suspension which comprises the steps of a) mixing coated particles comprising at least one pharmaceutically active substance having an unpleasant and/or bitter taste and optionally at least one excipient, with a suspension base comprising at least one osmotically active substance selected from the group consisting of sucrose, sorbitol, xylitol, erythritol, maltodextrin, cyclodextrin, potassium phosphate, sodium phosphate, sodium sulfate and sodium chloride, and mixtures thereof, and optionally at least one pharmaceutically acceptable excipient, to obtain a dry suspension mixture, wherein the amount of osmotically active substance is sufficient to provide a high osmolality to the admixture of said suspension base with an aqueous suspending medium in the ready-to-use suspension, and b) optionally filling the suspension mixture obtained in step a) into a container.

In another aspect, the present invention provides a process for preparing a ready-to-use suspension comprising the steps:

a) mixing coated particles comprising at least one pharmaceutically active substance having an unpleasant and/or bitter taste and optionally at least one excipient, with a suspension base comprising at least one osmotically active substance selected from the group consisting of sucrose, sorbitol, xylitol, erythritol, maltodextrin, cyclodextrin, potassium phosphate, sodium phosphate, sodium sulfate and sodium chloride, and mixtures thereof, and optionally at least one pharmaceutically acceptable excipient, to obtain a dry suspension mixture, wherein the amount of osmotically active substance is sufficient to provide a high osmolality to the admixture of said suspension base with an aqueous suspending medium in the ready-to-use suspension, and b) adding water to the dry suspension mixture obtained in step a) to form a ready-to- use suspension, and c) optionally filling the ready-to-use suspension into a container.

The ready-to-use suspension of the invention is palatable over at least 1 week, preferably at least 2 weeks.

Furthermore, the pharmaceutical compositions of the invention, e.g. the ready-to-use suspension, show a fast and quantitatively sufficient release of the active substance in the environmental conditions as found in the gastrointestinal tract which means good bioavailability.

An additional advantage of the pharmaceutical compositions of the invention is the omission of acidic components which offers much more freedom of choice for aromatisation, because it means that many aromas—otherwise incompatible with an acid taste—may be used for e.g. the suspensions of the invention.

Furthermore, also there is no need for addition of basic (i.e. alkaline) additives to the suspension base and/or the dry suspension mixture in cases where film-coatings which are soluble in an acid medium are used in the coated particles, said basic additives making aromatization even more difficult.

Finally, the suspension of the invention may be prepared by a simple production method thereby avoiding the costly and complicated preparative methods for taste-masking compositions of the prior art.

DETAILED DESCRIPTION OF THE INVENTION

Figure 1:
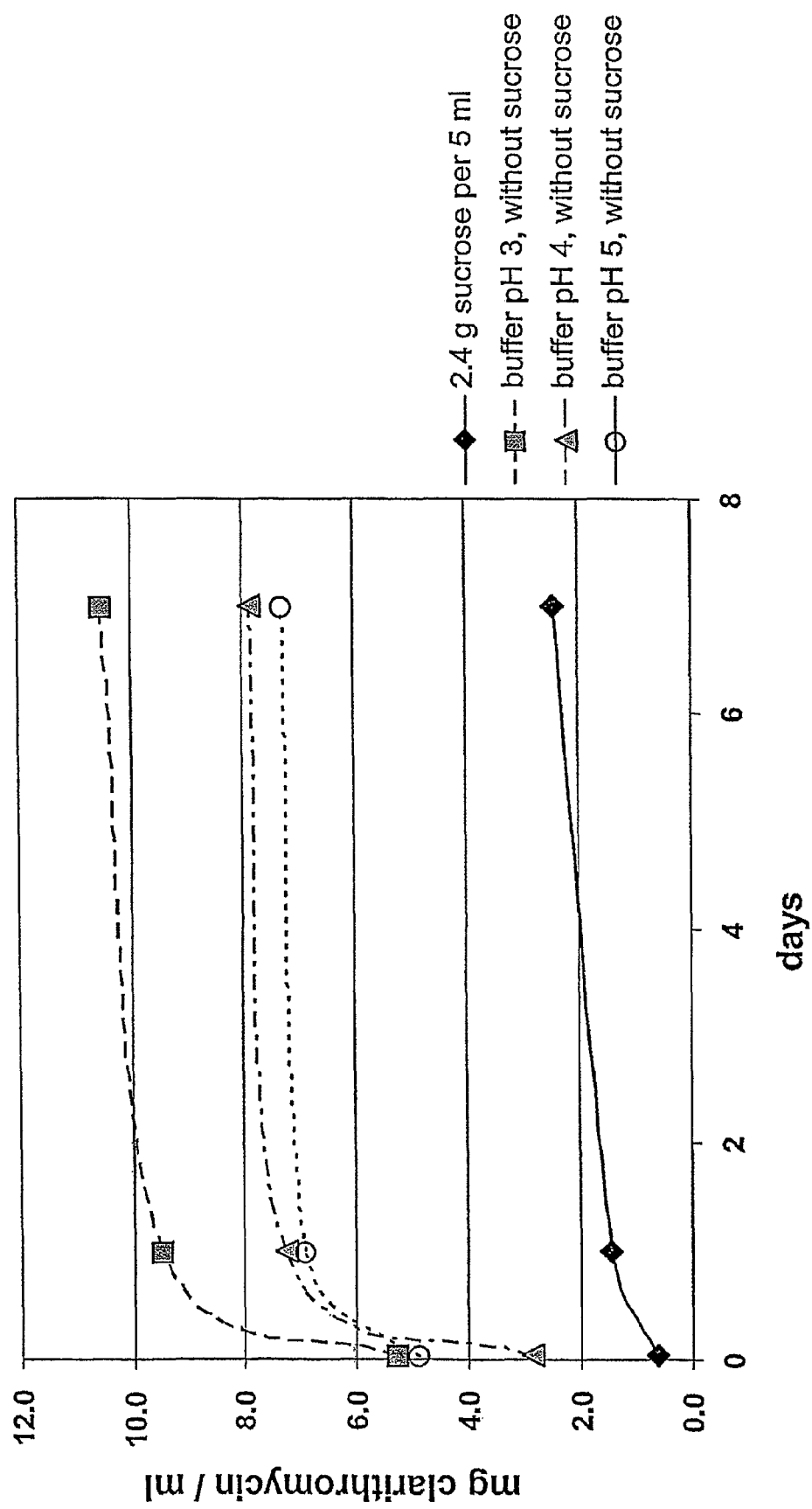
FIG. 1 shows the effect of high osmolality within a ready-to-use suspension as compared to the effect of the pH value alone on the leakage of clarithromycin from coated particles within a ready-to-use suspension

"Suspension" as herein used means—unless otherwise stated—a liquid formulation for oral administration which comprises coated, e.g. taste-masked, particles comprising at least one pharmaceutically active substance, and at least one pharmaceutically acceptable excipient, and which is prepared by dissolving or suspending a dry suspension mixture as herein described, e.g. in the form of a dry powder, in an aqueous vehicle, herein called the "suspending medium", before use for oral administration. Preferably the suspending medium is water.

The term "suspension base" as used herein is understood to mean a dry mixture of components comprising e.g. at least one osmotically active substance and optionally at least one pharmaceutically acceptable excipient, which may itself be mixed with e.g. taste-masked coated particles comprising an unpleasant and/or bitter tasting active ingredient, to form a "dry suspension mixture". Said "dry suspension mixture" may subsequently be dissolved or suspended in a suspending medium. The term "suspending medium" as herein used means the medium which is added to a dry suspension mixture to obtain the ready-to-use suspension which may subsequently be administered to the patient. Preferably, the suspending medium is aqueous, most preferably water. The term "reconstituted suspension" as herein used is understood to be synonymous to "ready-to-use" suspension.

The terms "functional coating" and "functional film-coating" as herein used are understood to include coatings which are soluble at a defined pH value, i.e. which are soluble in an environment having an acidic, or a neutral, or a basic pH value. Such functional coatings comprise enteric coatings or gastro-resistant coatings, and may additionally have taste-masking properties. Said functional coatings may be semipermeable, wherein the term "semipermeable" as herein used is understood to mean selectively permeable, i.e. allowing certain molecules to pass through the coating by diffusion.

The term "particles" as used herein refers to free flowing substances of any shape which are larger than a powder, such as crystals, beads (smooth, round or spherical particles), pellets, spheres, and granules.

The term "taste-masked" as used herein refers to any substance or particle, or oral pharmaceutical composition comprising an unpleasant tasting pharmaceutically active substance which has been treated to render it palatable and/or which does not substantially release the pharmaceutically active substance in the mouth, but rather for example in the stomach or the intestinal tract.

"An unpleasant and/or bitter taste" as used herein means that a majority of human patients judges said pharmaceutical composition or active substance therein comprised as having an unpleasant and/or bitter and/or extremely bitter taste after ingestion.

The coated particles which are comprised in the suspension of the invention may be prepared according to known methods, e.g. by conventional granulation techniques or extrusion and roller compacting techniques, applying e.g. a high sheer mixer, a compulsory mixer, e.g. of the type Diosna Collet Gral, a roller compactor, e.g. of the type Alexander Hutt, or an extruder, e.g. of the type Werner & Pfleiderer or Theyson, and may subsequently be coated. Alternatively, said particles may be obtained by applying known embedding techniques such as roller compacting or melt extrusion.

Said particles comprise at least one pharmaceutically active substance which has an unpleasant taste and/or bitter taste. Said active substances include, but are by no means limited to, antibiotics such as macrolides, e.g. erythromycin, clarithromycin, roxithromycin or azithromycin, fluoroquinolones such as ciprofloxacin and norfloxacin, cephalosporines, e.g. cefuroxime, ceftriaxone, or tetracyclic antibiotics such as chloramphenicol or chlorpromazine, or other antibacterial agents such as penicillin or ampicillin, analgesics, antihistaminics, decongestants, anti-inflammatory drugs, hypnotics, sedatives, tranquilizers, vitamins, enzymes, nutritional supplemements, hormones, and the like, including the pharmaceutically acceptable salts and esters thereof. Those with an extremely bitter taste such as macrolide antibiotics, especially erythromycin and clarithromycin, are particularly suited for the present invention. Therefore, said active substance is preferably a macrolide antibiotic such as erythromycin or one of its derivatives. Most preferably, the active substance is clarithromycin.

Said particles optionally further comprise at least one pharmaceutically acceptable excipient. The term "excipient" as used herein, refers to any substance which may be combined with an active ingredient for preparing convenient dosage forms, including, for example, wetting agents, diluents, binders, lubricants, disintegrants, colourings, flavors and sweeteners, and others as known in the art.

Examples of wetting agents are, for example polyoxyethylene polyoxypropylene block polymers, such as Poloxamer.

Suitable binders for use in the formulation of the invention include, but are not limited to, synthetic gums such as hydroxypropyl methylcellulose, polyvinyl pyrrolidone (povidone), carboxymethylcellulose, ethylcellulose and methylcellulose, starch, pregelatinized starch, gelatin, sugars (e.g., molasses) and natural gums (e.g., acacia gum, sodium alginate, panwar gum). Preferably, povidone (especially, Povidone USP) is used as the binder.

The herein mentioned particles may be covered with coatings, preferably functional coatings, e.g. functional film-coatings which may be soluble in an acidic, or in a neutral or in a basic pH value environment. Preferably said coatings, e.g. film-coatings, will start to dissolve at a pH value of more than about 4.5, e.g. said coatings are enteric or gastro-resistant coatings.

Alternatively, said coatings, e.g. film-coatings, may be pH independent.

The coating may be performed by applying a coating mixture to the particles by conventional methods, e.g. by spraying said coating mixture onto the particles. The coating—and optional drying—is preferably effected in a fluid bed coater, e.g. of the type Glatt Wurster or Huftlin Coater.

The coating mixture may comprise a coating component dissolved, dispersed or suspended in water or in an organic solvent, and optionally at least one excipient. Preferably, the coating component is a functional film-forming component, preferably an enteric film-forming component selected from the group comprising phthalates, such as cellulose phthalates, e.g. chemically modified cellulose phthalates such as hydroxypropylmethyl cellulose phthalate, cellulose acetate phthalate, or hydroxypropylmethyl cellulose acetate succinate, or poly(meth)acrylates, e.g. methacrylate polymers or copolymers, such as these commercially available under the trade mark Eudragit®, manufactured and marketed by Röhm GmbH & Co KG, Darmstadt, Germany. Examples of such methacrylic acid copolymers are described in USP/NF as "Methacrylic Acid Copolymer, Type A", such as commercially available under the trade mark Eudragit® L30 D55

(previously also named Eudragit® L 30 D) which is a copolymer of methacrylic acid and ethyl acrylate at a ratio of 1:1.

The functional film-coating may be soluble at an acidic pH value, i.e. may comprise a film-forming component soluble at an acidic pH value, e.g. acrylic polymers such as these commercially available under the trade mark Eudragit® E and Eudragit® EPO.

Optionally, the coating mixture may additionally comprise at least one excipient, e.g. a plasticizer, e.g. triethyl citrate.

In a specific embodiment of the invention coated particles are prepared according to the following method:

The particles are produced by way of spray agglomeration of clarithromycin and poloxamer, e.g. according to the method as described under the chapter "Fluidized Bed Granulators", in the Encyclopedia of Pharmaceutical Technology, Volume 7, Eds. James Swarbrick, James C. Boylan, 1993, pages 136 to 140. The mean particle size for the coating may range between 200 and 400 μm, e.g. between 250 and 350 μm, e.g. between 280 and 320 μm, e.g. between 290 and 310 μm, e.g. may be about 300 μm. Alternatively, the mean particle size for the coating may be up to about 500 μm, e.g. may range between 200 and 500 μm.

The coating may be applied according to conventional methods, e.g. in a fluid bed system, from an aqueous dispersion.

A typical composition of coated particles is described in Table 1 below:

TABLE 1

| Ingredient | Amount in g |
|---|---|
| Clarithromycin | 0.260 |
| Poloxamer | 0.096 |
| Eudragit L30D55 | 0.212 |
| Triethyl citrate | 0.032 |

The preparation of said particles and the use thereof for the preparation of the suspension of the invention are described in the Examples below.

The coated particles used in the compositions of the present invention may comprise the active substance in pharmaceutically effective amounts wherein said pharmaceutically effective amounts will depend on the active substance used. The term "pharmaceutically effective" as herein used is understood to include doses of said active substance which provide a desirable pharmacological effect.

Preferably, said coated particles comprise a macrolide, most preferably clarithromycin in an amount of about 5% to about 60% w/w, such as about 10% to about 50% w/w, e.g. about 15% to about 45% w/w, such as about 20% to about 40% w/w related to the coated particle.

The suspension of the invention may be prepared as follows: The coated particles are mixed with a suspension base comprising at least one osmotically active substance and optionally at least one pharmaceutically acceptable excipient, to form a dry mixture, i.e. the dry suspension mixture.

The term "osmotically active substance" as used herein is understood to mean a substance which dissociates in solution, e.g. when mixed with an aqueous suspending medium, e.g. with water, to form osmotically active particles. The osmotically active substances used for the invention are pharmaceutically acceptable.

Preferably, said osmotically active substance is characterized by being capable of reducing diffusion of the active substance molecules from the coated particles, by having a high solubility, e.g. in water, and by being physiologically, pharmacologically and orally acceptable.

Preferably, said osmotically active substance may comprise a carbohydrate, e.g. a polysaccharide, e.g. maltodextrin, or e.g. a cyclic polysaccharide, e.g. a cyclodextrin such as e.g. γ-cyclodextrin, an oligosaccharide, a disaccharide, e.g. sucrose, a monosaccharide, e.g. fructose or glucose, a carbohydrate-related compound such as a tetritol, e.g. erythritol, a pentahydric alcohol, e.g. xylit, or a hexahydric alcohol, e.g. sorbitol, or an inorganic salt such as potassium phosphate, sodium phosphate, sodium sulfate or sodium chloride, or mixtures thereof. Most preferably, the osmotically active substance is sucrose.

Preferably, said osmotically active substances are present in an amount of about 6% to 100% w/w, e.g. 20% to 90% % w/w, e.g. 40% to 80% w/w, e.g. 50% to 60% w/w, related to the suspending medium. Preferably, said osmotically active substances are present in an amount of about 85% to about 95% w/w, most preferably of about 89% w/w related to the suspending medium.

Preferably, said osmotically active substances may be present in amounts of about 3% to about 90%, e.g. about 15% to about 80%, such as about 20% to about 70%, e.g. about 30% to about 60%, such as about 40% to about 50% w/w related to the dry suspension mixture. More preferably, the osmotically active substances are present in amounts of about 70% to about 80% w/w in the case of carbohydrates, and about 3% to about 30% in case of an organic salts.

Optionally, the suspension base and/or the dry suspension mixture may additionally comprise at least one pharmaceutically acceptable excipient such as sugars, e.g. chemically modified, e.g. including fructose, glucose, sugar alcohols, sweeteners, e.g. nutritive and artificial, e.g. sodium saccharin, including aspartame, flow promoters, e.g. including silicium dioxides, e.g. colloidal, such as aerosils®, thickeners, e.g. guar flour, xanthan gum, methylcellulose;

binders, e.g. polyvinylpyrrolidones, celluloses flavoring agents, such as organic acids, e.g. citric acid, NaCl, natural and artificial flavours preservatives, such as potassium sorbate, sodium benzoate, dyestuffs (colorants) such as $TiO_2$, and fillers, surfactants, buffer substances, or other pharmaceutically acceptable excipients.

The dry suspension mixture, e.g. in form of a powder, may then optionally be filled into bottles or containers.

The dry suspension mixture may be suspended or dissolved in a suspending medium. Preferably, the suspending medium is aqueous, most preferably water. The resulting reconstituted suspension, i.e. ready-to-use suspension may optionally be filled into containers, e.g. bottles.

The amount of active substance incorporated in the coated particles present in the ready-to-use suspension may be about 1% to about 20% w/w, e.g. about 2% to about 15% w/w, such as about 3% to about 10% w/w, e.g. about 4% to about 8% w/w related to the ready-to-use suspension.

The ready-to-use suspension, more particularly, the admixture of the suspension base with the aqueous suspension medium, e.g. with water, shows a high osmolality of not less than about 2000 mosmol per kg of suspending medium, preferably per liter of water.

"High osmolality" as herein used is understood to mean an osmolality of more than 2000 mosmol per kg of suspension medium, e.g. per liter of water.

Preferably, the osmolality of said admixture of the suspension base with the aqueous suspending medium is not less than 2200 mosmol, e.g. more than about 2300 mosmol, e.g. more than about 2400 mosmol per kg of suspending medium, e.g. per liter of water. Most preferably, the osmolality is more than 2500 mosmol per kg of suspending medium, e.g. per liter of water.

Preferably, the osmolality of said admixture of the suspension base with the aqueous suspending medium is from about 2000 to about 4000 mosmol, such as from about 2200 to about 3800 mosmol, more preferably from about 2500 to about 3500 mosmol per kg of suspending medium, e.g. per liter of water.

Alternatively, the osmolality may be up to 4500 mosmol or more per kg of suspending medium.

The term "osmolality" as herein used is understood to mean the concentration of osmotically active particles of an osmotically active substance, i.e. a solute, e.g. molecules or ions thereof, in solution, i.e. in the liquid phase of a ready-to-use suspension, said liquid phase consisting essentially of the suspension base being mixed, i.e. dissolved or dispersed, in the suspending medium as herein described. Osmolality is generally expressed in mole of said solute per kg of solvent medium, e.g. in the present case, per kg of suspending medium, preferably per liter of water. A unit of osmolality is 1 osmol, indicating the amount of substance that dissociates in solution to form 1 mole of osmotically active particles. Osmolality may be measured according to known methods, such as those using a Vapor pressure Osmometer, a Freezing Point Depression Osmometer, or a Colloid Osmometer, according to the methods as described in Physikalische Chemie, Martin et al., ed. H. Stricker, Wissenschaftliche Verlagsgesellschaft, 1987. The osmolality may also be calculated according to the following calculation scheme:

osmolality [mosmol]=g of substance dissolved in 1000 g solvent medium divided by the molecular weight of said substance, the resulting quotient being first multiplied by the number of particles into which the dissolved substance dissociates and secondly multiplied by 1000.

In the present invention, dissolved substance means all substances which are dissolved in the liquid phase obtained after mixing the suspension base with the suspending medium, e.g. water, i.e. comprises osmotically active substances as herein defined and optionally other dissolved substances, e.g. as derived from the herein described excipients.

Preferably, the pharmaceutical compositions of the invention are provided either as a dry suspension mixture to be used to prepare aqueous suspensions or dispersions, or as ready-to-use suspensions. However, it is envisaged to be within the scope of the invention that the dry suspension mixture may also be used to prepare other dosage forms such as chewable preparations, soluble tablets or effervescent tablets or the like, or mono-dose sachets.

The ready-to-use suspension of the invention is palatable and maintains its palatability even over a prolonged period of time, i.e. over at least 1 week, preferably at least 2 weeks, e.g. 4 weeks, after being reconstituted with e.g. water, preferably e.g. over a whole duration of therapy.

The degree of palatability of the suspension can be measured indirectly by determining the amount of active substance, e.g. of clarithromycin, which is dissolved in the suspension at room temperature according to known methods applying HPLC, for example as described in the European Pharmacopoea $3^{rd}$ edition, 1997, and Supplement 2000. Said amount of dissolved active substance directly correlates to the bitterness of the suspension as can be seen e.g. in WO 93/12771. Alternatively, palatability can be judged by trained flavour specialists, e.g. as described in the patent application mentioned above.

Without intending to be limited by theory, the inventors believe that the considerable improvement of the taste which is observed with the suspensions of the invention is due to the high osmolality of the liquid medium surrounding the suspended particles which seems to lead to a decrease in the diffusion of the active substance into the admixture of the suspension base with the suspending medium, i.e. to a reduction and/or elimination of leakage of the active substance.

It has surprisingly been found by the inventors that the omission of certain conventional additives such as acidic and/or basic additives from suspensions of coated particles, e.g. enteric coated particles, may substantially improve the taste of suspensions comprising said particles, possibly due to reduced diffusion.

The high level of osmolality within the suspension avoids the necessity of an adjustment of the pH value of the suspension by way of adding acids, bases and/or acid or basic salts (depending on the type of functional coating used) to protect the taste-masking coatings from dissolution. Despite the fact that the coating is actually soluble at the pH value of the suspension, it does not dissolve; again without intending to be limited by theory, it is believed that this is due to the fact that there are no ions available for the salt formation which is necessary for the dissolution. Therefore, the pharmaceutical compositions of the invention as described above may also be essentially free of acidic or basic additives, such as organic acids, e.g. citric acid. The lack of acidic or basic additives in pharmaceutical compositions of the invention allows for much better conditions for successful aromatization as compared to conventional compositions which comprise said additives.

Preferably, the suspension of the present invention shows a fast dissolution at a pH value of 6.8, which means 80% of the active substance are dissolved within 15 minutes measured by the dissolution test according to the US Pharmacopoea USP 27-NF 22 S2, 2004. This means that the active substance is released in sufficient quantity at an acceptable rate in the gastrointestinal tract, which generally indicates good bioavailability.

The following Table 2 shows how the osmolality can be adjusted by using mixtures of different osmotically active substances as mentioned before (osmolality is calculated as described above):

TABLE 2

| | Amounts in g | | | |
|---|---|---|---|---|
| Saccharose | 100 | | 50 | 95 |
| Glucose | | 50 | | |
| Fructose | | | | 30 |
| Sorbit | | | | 25 |
| Erythritol | | | 30 | |
| $K_3PO_4$ | | | 5 | |
| $Na_3PO_4$ | | | | 3 |
| $Na_2SO_4$ | | | | 3 |

TABLE 2-continued

| | Amounts in g | | | | | | | |
|---|---|---|---|---|---|---|---|---|
| NaCl | | | | | 6 | | | 5 |
| Water | 100 | 100 | 100 | 100 | 100 | 100 | 100 | 100 |
| Osmolality [mosmol] | 2921 | 2775 | 2457 | 2403 | 2053 | 2397 | 2011 | 4486 |
| Concentration* [w/w %] | 50% | 33% | 23% | 35% | 6% | 25% | 22% | 50% |
| Concentration** [w/w %] | 100% | 50% | 30% | 55% | 6% | 33% | 28% | 100% |

*concentration related to the solution
**concentration related to the suspending medium The pharmaceutical compositions of the invention may be used as a medicament.

In one aspect, the pharmaceutical compositions of the invention may be used in the preparation of a medicament for the treatment and/or prophylaxis of infectious diseases.

In a further aspect, the present invention provides a method for the treatment and/or prophylaxis of infectious diseases, especially microbial diseases, such as bacterial diseases and chlamydial diseases, and certain complications thereof, in a human or non-human mammal which comprises administering a therapeutically effective, non-toxic, amount of the active substance comprised in the pharmaceutical composition of the invention to a human or non-human mammal in need thereof. Said active substance is preferably a macrolide, most preferably clarithromycin. The term "therapeutically effective" as herein used is understood to include amounts of said active substance which provide a desirable therapeutical effect.

In the treatment and/or prophylaxis of infectious diseases and certain complications thereof, the suspension of the invention may comprise a pharmaceutically effective amount of the active substance as herein described, preferably of clarithromycin, in the dosage range usually used for prophylaxis and/or treatment of infectious diseases.

The suspension of the invention is particularly suitable for patients who have difficulty swallowing, such as children and elderly patients.

The present invention also provides a kit of parts comprising
a component a) comprising coated particles comprising at least one pharmaceutically active substance having an unpleasant and/or bitter taste and optionally at least one excipient, and
a component b) comprising a suspension basis comprising at least one osmotically active substance which is capable of providing a high osmolality to the admixture of said suspension basis with an aqueous suspending medium in the ready-to-use suspension, and optionally
a component c) comprising at least one pharmaceutically acceptable excipient, for separate, sequential or simultaneous administration. Said kit of parts may additionally comprise a component d) being an aqueous suspending medium, e.g. water. Components a), b), c) and d) may be packaged in a single container or in 2 or more separate containers. When stored in separate containers, the components a), b), c) and d) may be admixed before administration.

The following Examples are provided to further illustrate the invention without, however, limiting the invention:

EXAMPLES

The coated particles are produced by way of spray agglomeration of clarithromycin and poloxamer. The mean particle size for the coating ranges between 200 and 400 μm. The coating is applied in a fluid bed system from an aqueous dispersion. The composition of the particles is seen in Table 1:

TABLE 1

| Ingredient | Amount in g |
|---|---|
| Clarithromycin | 0.260 |
| Poloxamer | 0.096 |
| Eudragit L30D55 | 0.212 |
| Triethyl citrate | 0.032 |

The suspensions of Examples 1 to 6 are prepared as follows:

The coated particles as from Table 1 are mixed with the ingredients as listed below in Table 3 or in Table 4, to form a dry suspension mixture, which is subsequently suspended by adding the indicated amount of water.

The portion of active substance which is dissolved in the aqueous suspension is determined at different moments in time by HPLC. The amount of said dissolved portion correlates with the bitter taste experienced by patients after having ingested said suspension.

Examples Group A

The composition of the suspension for Examples 1 to 4 are found in Table 3 below:

TABLE 3

| | Example | | | |
|---|---|---|---|---|
| | 1 | 2 | 3 | 4 |
| | pH value of the suspension | | | |
| Ingredients | pH 4.5 | pH 3 | pH 4 | pH 5 |
| Coated particles (of Table 1) | 0.600 | 0.600 | 0.600 | 0.600 |
| Powdered sucrose (Ph. Eur.) | 2.400 | | | |
| Flavour (Fruit essence*) | 0.075 | 0.075 | 0.075 | 0.075 |
| Citric acid anhydrate** | 0.003 | ad 3 | ad 4 | ad 5 |
| Water for preparing the suspension | 2.714 | 2.714 | 2.714 | 2.714 |
| mOsmol (calculated) | 2583 | 120 | 140 | 150 |

Values are amounts in g
*Flavour used is mixed fruits powdery flavour, commercially available as 204264 H&R
**citric acid is dissolved in water and added to titrate towards the desired indicated pH value The impact of the osmotic conditions on the enteric coating, i.e. taste-mask coating of the particles of Table 1, is determined by measuring the amount of clarithromycin dissolved at room temperature. This is a measurement of the tightness of said coating as well as indirectly a measurement of the bitterness of the suspension. The results are seen in FIG. 1 which shows that the presence of 2.4 g sucrose per 5 ml of suspension drastically reduces the leakage of clarithromycin from the coated particles when compared to suspensions without sucrose. Less dissolved clarithromycin means less bitter taste of the suspension, i.e. means that said suspension is palatable.

Surprisingly, an acidic pH-value alone—which is generally thought to prevent the dissolution of the enteric coating—does nevertheless not prevent clarithromycin from leaking into the suspension. The presence of a high osmolality (see Example 1) is, however, sufficient to prevent leakage of clarithromycin regardless of the pH-value in the range seen in FIG. 1.

Examples Group B

The composition of the suspension for Examples 5 to 7 are found in Table 4 below:

TABLE 4

| | Example | | |
|---|---|---|---|
| Ingredients | 5 | 6 | 7 |
| Coated particles (of Table 1) | 0.600 | 0.600 | 0.600 |
| Powdered sucrose (Ph. Eur.) | | 2.400 | |
| Fructose | | | 1.200 |
| Glucose | | | 1.200 |
| Water for preparing the suspension | 2.714 | 2.714 | 2.714 |
| mOsmol (calculated) | <5 | 2583 | 4868 |

Values are amounts in g

Figure 2:
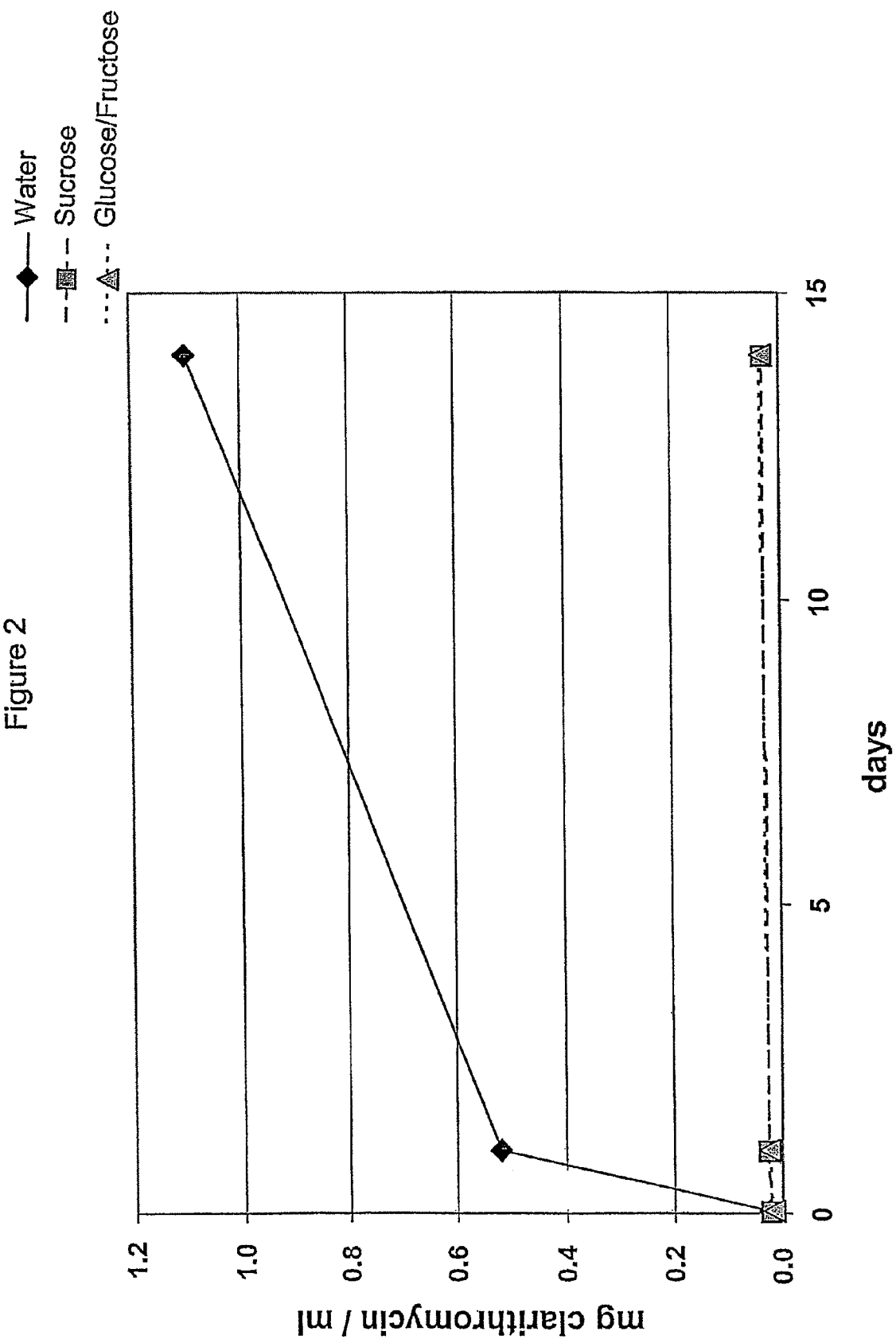
FIG. 2 shows the effect of the presence of different osmotically active substances on the leakage of clarithromycin within a suspension

The impact of the osmotic conditions on the enteric coating, i.e. taste-mask coating of the particles of Table 1, is again determined by measuring the amount of clarithromycin dissolved at room temperature; the results are seen in FIG. 2 which shows that the addition of sucrose or a mixture of glucose and fructose prevents clarithromycin from leaking out of the coated particles. This is believed to be due to the high osmolality of the corresponding suspensions, more particularly, of the admixture of the suspension base with water, which is more than 2500 mosmol per liter of water.

The invention claimed is:

1. A pharmaceutical composition for oral administration comprising
   a) coated particles comprising at least one pharmaceutically active substance having an unpleasant and/or bitter taste and optionally at least one excipient, and
   b) a suspension base comprising at least one osmotically active substance which is capable of providing a high osmolality to an admixture of said suspension base with an aqueous suspending medium in a reconstituted suspension, and
   c) optionally at least one pharmaceutically acceptable excipient, wherein said high osmolality is from about 2000 to about 3800 mosmol per kg of the suspending medium.

2. The pharmaceutical composition according to claim 1 wherein the coated particles are taste-masked.

3. The pharmaceutical composition according to claim 1 wherein said high osmolality is not less than 2500 mosmol per kg of suspending medium.

4. The pharmaceutical composition according to claim 1 in the form of a dry powder.

5. A pharmaceutical composition in the form of a reconstituted suspension which is prepared by suspending the pharmaceutical composition of claim 1 in an aqueous suspending medium.

6. The pharmaceutical composition according to claim 5 wherein the aqueous suspending medium is water.

7. The pharmaceutical composition according to claim 1 wherein the osmotically active substance is selected from the group consisting of sucrose, sorbitol, xylitol, erythritol, maltodextrin, cyclodextrin, potassium phosphate, sodium phosphate, sodium sulfate and sodium chloride, and mixtures thereof.

8. The pharmaceutical composition according to claim 5 wherein the amount of the osmotically active substance is from about 6% to about 100% w/w related to the suspending medium.

9. The pharmaceutical composition according to claim 5, wherein the amount of the osmotically active substance is from about 85% to about 95% w/w related to the suspending medium.

10. The pharmaceutical composition according to claim 5, wherein the amount of the osmotically active substance is about 89% w/w related to the suspending medium.

11. The pharmaceutical composition according to claim 5 wherein the aqueous suspending medium is water and wherein the osmolality of the admixture of the suspension base with water is not less than 2000 mosmol per litre.

12. The pharmaceutical composition according to claim 1, wherein the at least one pharmaceutically active substance is clarithromycin.

13. The pharmaceutical composition according to claim 1, which is essentially free of an acidic and/or basic additive.

14. A method for preparing a pharmaceutical composition as defined in claim 1 which comprises the steps of
   a) mixing said coated particles with said suspension base comprising at least one osmotically active substance selected from the group consisting of sucrose, sorbitol, xylitol, erythritol, maltodextrin, clodextrin, potassium phosphate, sodium phosphate, sodium sulfate and sodium chloride, and mixtures thereof, and optionally at least one pharmaceutically acceptable excipient, to obtain a dry suspension mixture, wherein the amount of osmotically active substance is sufficient to provide a high osmolality to the admixture of said suspension base with an aqueous suspending medium in the ready-to-use suspension, and
   b) optionally filling the suspension mixture obtained in step a) into a container.

15. A method for preparing a pharmaceutical composition as defined in claim 1 comprising the steps of
   a) mixing said coated particles with said suspension base comprising at least one osmotically active substance selected from the group consisting of sucrose, sorbitol, xylitol, erythritol, maltodextrin, cyclodextrin, potassium phosphate, sodium phosphate, sodium sulfate and sodium chloride, and mixtures thereof, and optionally at least one pharmaceutically acceptable excipient, to obtain a dry suspension mixture, wherein the amount of osmotically active substance is sufficient to provide a high osmolality to the admixture of said suspension base with an aqueous suspending medium in the ready-to-use suspension, and
   b) adding water to the dry suspension mixture obtained in step a) to form a ready-to-use suspension, and
   c) optionally filling the ready-to-use suspension into a container.

16. A pharmaceutical composition for oral administration comprising:
   a) coated particles comprising at least one pharmaceutically active substance having an unpleasant and/or bitter taste and optionally at least one excipient, and
   b) a suspension base comprising at least one osmotically active substance which is capable of providing an osmolality of from about 2500 to about 3800 mosmol per kg of suspending medium to an admixture of said suspension base with an aqueous suspending medium in a reconstituted suspension containing at least said coated particles and said suspension base, and
   c) optionally at least one pharmaceutically acceptable excipient,
   wherein the pharmaceutical composition is provided in the form of a dry powder.

17. The pharmaceutical composition according to claim 16 wherein the coated particles are taste-masked.

18. The pharmaceutical composition according to claim 16, wherein the at least one pharmaceutically active substance is clarithromycin.

19. A pharmaceutical delivery system comprising a container including within the container a reconstituted suspension containing a composition according to claim 16 wetted out therein.

* * * * *